United States Patent [19]

Young et al.

[11] Patent Number: 5,063,917
[45] Date of Patent: Nov. 12, 1991

[54] LIMB BRACE OR IMMOBILIZER

[75] Inventors: David E. Young, Watlington; Kenneth P. Davis, High Wycombe, both of England

[73] Assignee: Protectair Limited, Abingdon, England

[21] Appl. No.: 548,612

[22] Filed: Jul. 5, 1990

[30] Foreign Application Priority Data

Aug. 14, 1989 [GB] United Kingdom ............... 8918519
Aug. 25, 1989 [GB] United Kingdom ............... 8919400

[51] Int. Cl.$^5$ ............................................... A61F 5/00
[52] U.S. Cl. ................................. 128/80 R; 128/80 F; 128/87 R
[58] Field of Search ...................... 128/77, 80 R, 80 C, 128/80 F, 80 H, 878, 87 R, 88, 89 R, 90, 102.1, 103.1, 105.1, 121.1, 123.1, 124.1, 125.1, 126.1; 24/200

[56] References Cited

U.S. PATENT DOCUMENTS

| 948,305 | 2/1910 | Bunker | 128/126.1 |
| 3,024,784 | 3/1962 | Monfardini | 128/87 R |
| 4,019,504 | 4/1977 | Sterling | 128/88 |
| 4,428,369 | 1/1984 | Peckham et al. | 128/80 C |
| 4,681,097 | 7/1987 | Pansiera | 128/77 |
| 4,776,326 | 10/1988 | Young et al. | 128/80 F |
| 4,941,465 | 7/1990 | Borschneck | 128/87 R |

FOREIGN PATENT DOCUMENTS

| 12702 | of 1899 | United Kingdom | 128/125.1 |
| 505775 | 5/1939 | United Kingdom | |
| 2130488 | 6/1984 | United Kingdom | |
| 2177603 | 1/1987 | United Kingdom | |
| 2182714 | 5/1987 | United Kingdom | |

OTHER PUBLICATIONS

"The Tracker Knee Brace," Depuy promotional literature copyrighted 1984.
"Introducing Zimmer Flex 10," Zimmer promotional literature copyrighted 1986.

Primary Examiner—Richard J. Apley
Assistant Examiner—Linda C. M. Dvorak
Attorney, Agent, or Firm—Tilton, Fallon & Lungmus

[57] ABSTRACT

A limb brace or immobilizer having at least two relatively rigid support arms extending medially and laterally along opposite sides of a wearer's limb, each support arm having a limb-contacting plate of arcuate cross-sectional configuration and a traction plate connected to or formed integrally with the limb-contacting plate. Each traction plate has a pair of wing portions extending anteriorly and posteriorly in relation to the limb-support arm and spaced outwardly from the limb-contacting plate, with the span of the wing portions being substantially less than the anterior-posterior dimensions of the associated limb-contacting plate. Attachment straps are adjustably secured to the wing portions and join corresponding wing portions of the traction plates on opposite sides of a wearer's limb to secure the assembly in limb-bracing or limb-immobilizing condition.

10 Claims, 2 Drawing Sheets

LIMB BRACE OR IMMOBILIZER

BACKGROUND AND SUMMARY

Limb immobilisers and braces for limbs and joints are well known. An immobiliser may consist of nothing more complex than a relatively rigid member bound to a limb with tape or bandages, or it may be more elaborate with numerous reinforcements, flaps, pads, and pockets.

Braces, such as knee braces, also are available in many types and varying degrees of complexity. Several are described in co-owned UK patent GB 2,130,488B, U.S. Pat. Nos. 4,467,792 and 4,559,935, and European patent 0109847. A further detailed discussion of the art is given in published UK specification GB 2,182,714A. A modular bracing system is also disclosed in co-owned published application GB 2,177,603B and U.S. Pat. No. 4,776,326.

We are also aware of a knee brace marketed by DePuy Inc. of Warsaw, Ind., U.S.A., that has medial and lateral hinges and proximal and distal hinge arms. A leg-contacting shell is carried by each of the arms with the calf shells being fixed in place but the thigh shells being slidably connected to the proximal arms. Specifically, a hole near the upper end of each proximal arm is threaded and each thigh shell has a central slot extending along a part of the length thereof. A turnscrew is slidably retained in the slot and can be tightened to lock each thigh shell in a selected position along the proximal arm on which it is mounted.

A knee brace by Zimmer Incorporated of Charlotte, N.C., U.S.A., marketed as the "LM 10" brace, also utilizes the slotted sliding shell principle. In both the DePuy and Zimmer braces, the shells appear to be of relatively thin plastics material and the provision of slots, for slidable attachment to the proximal arms, increases their weakness. In addition, both braces use circumferential hook and loop material straps to secure them to patients. A disadvantage of such a strapping system is that a brace may move or "gape" under the straps during flexion; this amounts to failure of the brace to exert control of the joint. Immobilisers with such strapping systems are also liable to be overridden by strong vigorous patients.

Another disadvantage of existing constructions is that the attachment straps are commonly connected to edge portions of the flexible shells. Tensioning of the straps may result in an undesirable application of forces transmitted to and by certain portions of the shells and also to the possibility that such tensioning, either during application or wearer movement, may result in shell failure.

An important aspect of this invention therefore lies in providing an adjustable immobiliser or brace in which the shells or limb-contacting plates may be easily extended or retracted without, at the same time, resulting in a construction that presents a substantial risk of failure under conditions of vigorous use. Donning and doffing of the device may be easily and quickly achieved without requiring the wearer to step into or through the device.

A particularly important aspect of the invention lies in providing an adjustable brace/immobiliser construction in which loadings are distributed and are not directly applied by the attachment straps to the edges of the limb-contacting plates or shells. Instead, flexible traction plates are joined directly to the straps and in turn exert centrally-directed forces against the limb-contacting plates which then distribute those forces against medial and lateral surfaces of the limb. While the anterior/posterior edges of the limb-contacting plates do not function as strap-attachment zones, they may nevertheless perform a protective function in shielding the limb against direct contact by the tensioned straps.

Briefly, a limb brace or immobiliser embodying this invention includes at least two relatively rigid support arms adapted to extend medially and laterally along opposite sides of a wearer's limb in the vicinity of a joint. In the case of a brace, the support arms are connected to hinges along with a second set of support arms, thereby permitting controlled movement at the joint, whereas in the case of an immobiliser, the support arms are unjointed and, when worn by a patient, lock the joint against flexion and extension. Whether the invention is utilized with a limb brace or a limb immobiliser, there must be at least one medial limb support arm and at least one lateral limb support arm.

First and second limb-contacting plates of arcuate cross-sectional configuration are connected to the two support arms. At least two traction plates, which may also be referred to as drawbar plates, are associated with the limb-contacting plates, each traction plate having a pair of wing portions extending anteriorly and posteriorly with respect to a limb support arm and being spaced outwardly from the limb-contacting plate associated therewith. The span of the wing portions of each traction plate is substantially less than the anterior-posterior dimension of the associated limb-contacting plate. Attachment straps are adjustably secured to the wing portions and join corresponding wing portions of the traction plates on opposite sides of a wearer's limb to secure the assembly in limb-bracing or limb-immobilising condition. Since each traction plate is centrally joined to or merged with a limb-contacting plate, forces exerted by the tightened straps are applied centrally to the limb-contacting plates and are then distributed against the limb by the flexible limb-contacting plates. The traction plates are most advantageously formed of stiff but flexible thermoplastic material so that their wing portions, which normally angle outwardly away from the central portions, may flex inwardly under the tensioning forces applied by the straps. Flexure of the wing portions, and their capability of returning to their original positions when tensioning forces are wholly or partially relieved, results in a cushioning action that helps maintain the brace/immobiliser in position without excessive tightening of the straps. Since the anterior/posterior edges of the traction plates are spaced well inboard from the edges of the associated limb-contacting plates, the limb-contacting plates may perform a shielding function in preventing or reducing direct contact between the attachment straps and the patient's limb.

Other features, advantages, and objects of the invention will become apparent from the specification and drawings.

DRAWINGS

DETAILED DESCRIPTION OF PREFERRED EMBODIMENTS

Figure 1:
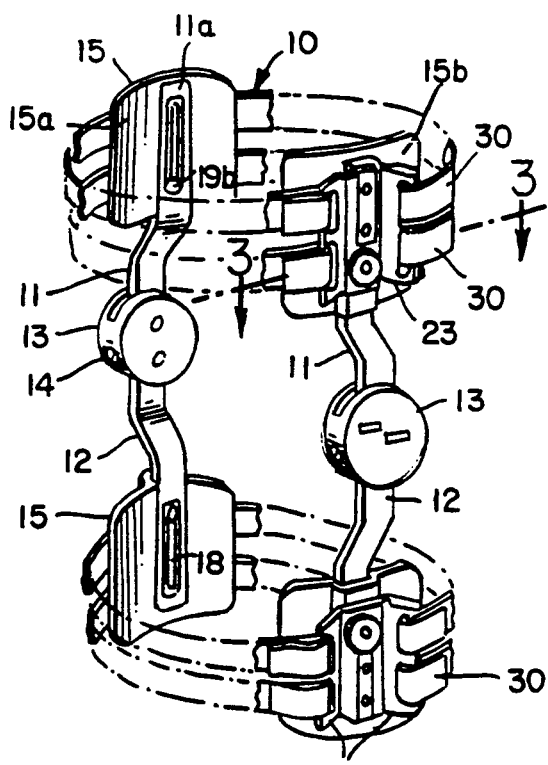
FIG. 1 is a side perspective view of a knee brace showing the means for securing the brace to a wearer's leg.

FIG. 1 illustrates a knee brace 10 embodying the features of this invention. Upper and lower support arms or bars 11 and 12 are pivotally connected to a pair of hinge bodies 13 to provide bi-pivotal hinge assemblies for bracing a patient's limb at the knee joint. Preferably the hinge assemblies are adjustable to control the extent of flexion and extension, all as well known in the art. If such assemblies are adjusted by screws 14 to prevent relative movement of arms 11, 12, then the hinge assemblies are inactivated and function as limb immobilisers. It is to be understood that if the only desired function is limb immobilisation, then the hinge bodies 13 may be entirely eliminated and arms 11, 12 may be permanently joined or integrally formed.

Each arm 11, 12 is provided at its free end with a limb-contacting plate 15. Four identical plates 15 are shown in the particular embodiment depicted in FIG. 1 although for purposes of an operative combination only two such plates on opposite sides (medial and lateral) of a wearer's limb would be necessary for realizing the advantages of the invention. Each limb-contacting plate is generally rectangular in outline and has a recessed central portion 16 defining a longitudinally-elongated cavity 17 for slidably receiving an end portion 11a of arm 11 (or 12). As shown most clearly in FIG. 2, each arm is longitudinally slotted at 18 for receiving the shank 19a of an adjustment screw 19. The head 19b of the screw is received in an enlarged recess 20 formed about slot 18, the parts being dimensioned so that axial outward movement of the screw in relation to arm 11 (or 12) is prevented without, at the same time, preventing sliding movement of the screw along the length of slot 18.

The shank 19a of screw 19 extends through an opening 21 in the limb-contacting plate 15 and then through a coaxial opening 22 in traction plate or drawbar plate 23. A turnwheel 24 threadedly receives the shank of the screw so that when the turnwheel is tightened screw 19 will be secured in a selected position of adjustment along the length of slot 18.

Figure 2:
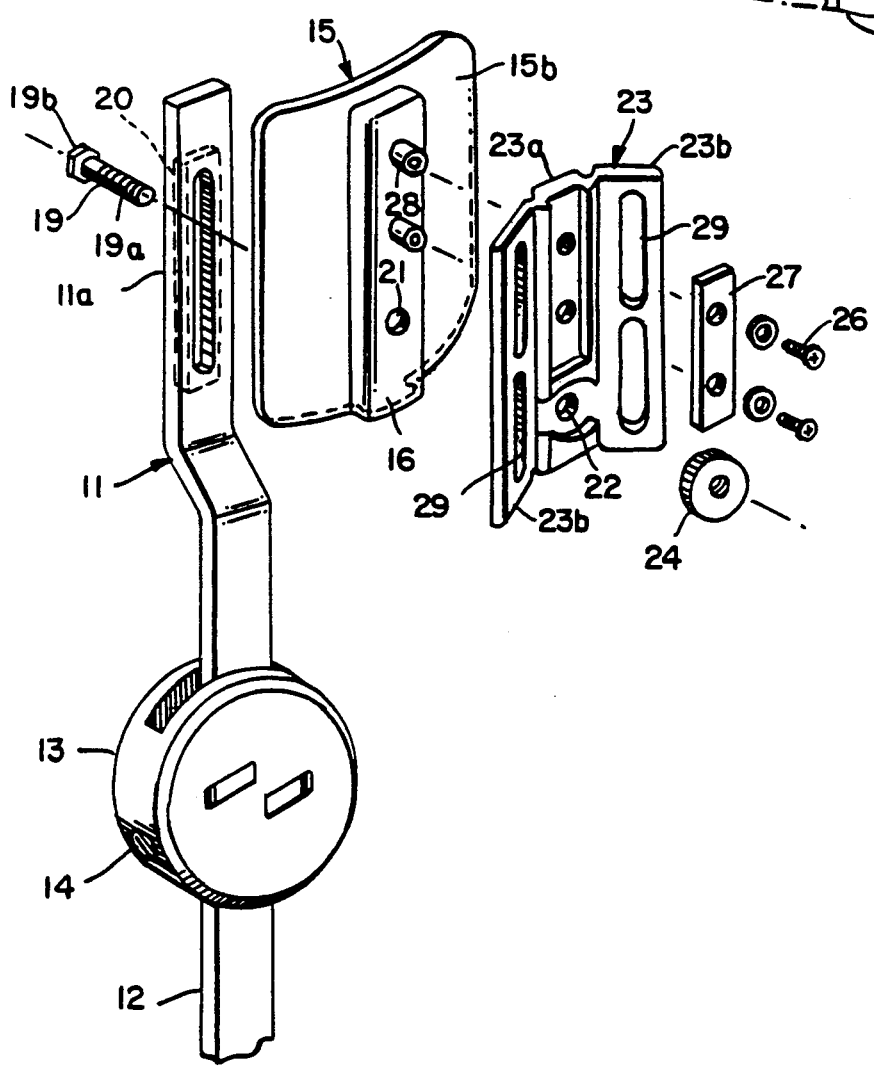
FIG. 2 is an exploded fragmentary perspective view illustrating major components of the invention.
Figure 3:
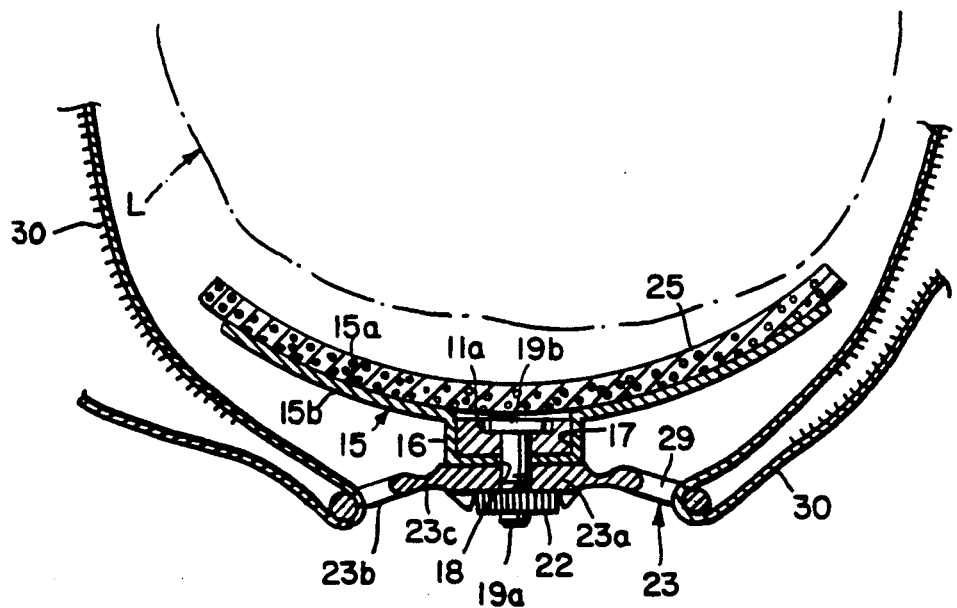
FIG. 3 is a greatly enlarged horizontal sectional view taken along line 3—3 of FIG. 1 and showing a brace-/immobiliser assembly before tightening of the attachment straps.

Viewed from above or in transverse section, the limb-contacting plate 15 is of arcuate configuration with a concave inner surface 15a facing towards the patient's limb and a convex outer surface 15b facing away from that limb. As shown in FIGS. 2 and 3, each limb-contacting plate is relatively thin. While various fabricating materials may be used, particularly effective results have been achieved where the limb-contacting plates 15 are formed of a stiff but nevertheless flexible thermoplastic material such as nylon 6. Other plastics materials having similar properties, such as, for example, polypropylene or acrylonitrile-butadiene-styrene, might also be used. If desired, the inner surface 15a of the limb-contacting plate may be lined with a cushioning layer 25 (FIG. 3). The cushioning layer may be formed of any of a wide variety of resilient, compressible materials although a thermoplastic foam, such as polyether foam is believed preferable.

Each traction plate 23 has a central portion 23a and a pair of wing portions 23b. As shown in the drawings, the traction plate is mounted so that its wing portions 23b extend anteriorly and posteriorly from arm 11 (or 12) and from the longitudinal midlines of plates 15 and 23. In the embodiment of FIGS. 1-4, central portion 23a is rigidly secured to the outer side of recessed portion 16 of limb-contacting plate 15 by means of screws 26 which pass through apertures in rigid mounting member 27 and in central portion 23a, and are threadedly received in integral protuberances 28 of limb-contacting plate 15.

Wing portions 23b are slotted at 29 to receive attachment straps 30. Such straps may be formed of any suitable non-stretchable fabric and may utilize hook and loop fastening means for securing the ends of the straps in fastened condition. Alternatively, the attachment straps may be provided with buckles or any other conventional attachment means. If desired, such straps may be equipped at their ends with drawbar elements having hook portions received in the slots 29 of wing portions 23b. The particular means for joining the straps to the wing portions of the traction plates is not critical as long as such means allows the straps to encircle a limb as indicated in FIG. 1. Thus, a basic operative combination embodying the invention would include straps 30 extending from the wing portions of one traction plate 23 located, for example, on the medial side of a patient's limb, to the wing portions of a second traction plate located on the lateral side of that limb. By tightening the straps, the opposing concave faces 15a of the limb-contacting plates 15 that are associated with the two traction plates 23 are drawn into firm supportive contact with the limb.

Like the limb-contacting plate 15, traction plate 23 is formed from a stiff but nevertheless flexible material. The same materials used for the plates 15 may also be used for plates 23. Of particular importance are the facts that when the traction plate 23 is in a relaxed or untensioned state, wing portions 23b angle outwardly away from the outer surface 15b of limb-contacting plate 15, and that the maximum span of wing portions 23b is substantially less than the anterior-posterior dimension of limb-contacting plate 15. Also, it will be observed that wing portions 23b are spaced a substantial distance from the convex surface 15b of plate 15 because of the recessed portion 16 of that plate. As a result, during application of a brace or immobiliser to a wearer's limb, the slots 29 of, wing portions 23b are readily accessible for insertion of straps 30, even by a patient having limited dexterity.

Figure 4:
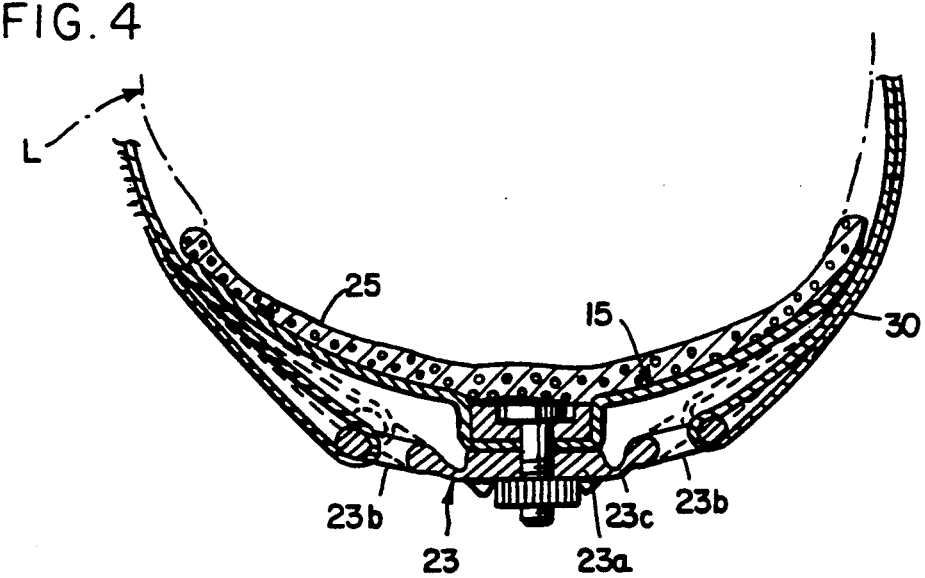
FIG. 4 is a sectional view similar to FIG. 3 but depicting the assembly following tightening of the attachment straps.

Tightening of the straps produces the effects somewhat schematically illustrated in FIG. 4. The thickness of material of each traction plate is reduced along two parallel zones 23c to form integral hinge lines allowing a spring-like inward flexing action of the wing portions 23b as the straps are tightened. The forces exerted by the straps are therefore transmitted directly to the traction plate 23 connected by its central portion 23a to the mid-portion 16 of limb-contacting plate 15. The limb-contacting plate in turn tends to distribute the forces against the wearer's limb L. Inward flexure of wing portions 23b makes them less subject to possible contact by other objects but, more importantly, such inward flexure tensions the traction plate 23 so that the wing portions can flex further inwardly, or flex partially outwardly, in response to extraordinary forces that might be transmitted by the straps during patient movement or treatment. For example, should patient exertion result in muscular expansion, that expansion may be at least partially accommodated to cushion the constrictive force of the straps by limited inward flexing movement of wing portions 23b from the solid-line positions to the broken line positions depicted in FIG. 4.

It will also be observed that because the traction plate 23 is substantially narrower than the limb-contacting plate 15, the flexible edge portions of plate 15 may perform a shielding function in reducing the possibility of abrading contact between straps 30 and the patient's limb L adjacent the outer edges of the limb-contacting plate. In other respects, however, the flexible limb-contacting plate is generally free to flex and conform with the contour of a patient's limb without distortions that might otherwise be caused by forces exerted directly against the patient contacting plate by the attaching straps.

It is believed apparent from the foregoing that setting up of the assembly is made especially easy by the preferred construction of arcuate limb-contacting plates with large-radius traction plates which have inherent flexibility and are also arranged that a limb will be loaded evenly. In addition, it is unnecessary with the instant invention to fully dismantle the strapping connections in order to make adjustments since the turnwheels remain exposed at all times.

Referring again to FIG. 1, it will be observed that the upper traction plates 23 are connected to a pair of anterior straps 30 and also to a pair of posterior straps 30, and a similar arrangement is provided with regard to the lower traction plates 23. With such an arrangement, it has been found that if one strap of each pair is non-stretchable and the other strap of the same pair has at least limited elasticity, particularly effective results are achieved in the treatment of certain injuries such as, for example, damaged posterior or anterior cruciate ligaments. The alternative pairings of inelastic and elastic straps helps insure against undesirable movement of the brace in relation to the limb during patient movement.

Figure 5:
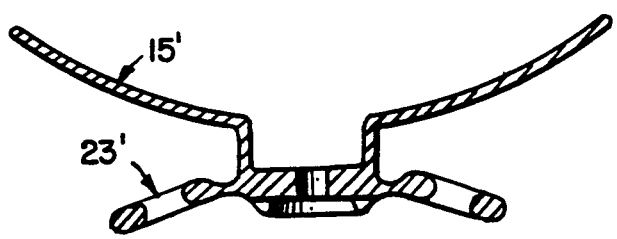
FIG. 5 is a sectional view of a second embodiment of the invention in which the limb-contacting plate and traction plate are integrally formed.

FIG. 5 depicts a modification of the structure illustrated in FIGS. 1-4. In the modified construction, traction plate 23' and limb-contacting plate 15' are integrally formed rather than being composed of separate elements permanently connected together. In all other respects, the modification is similar in structure and operation to the embodiment of FIGS. 1-4.

While in the foregoing we have disclosed embodiments of the invention in considerable detail for purposes of illustration, it will be understood by those skilled in the art that many of these details may be varied without departing from the spirit and scope of the invention.

We claim:

1. A limb brace/immobiliser comprising at least two rigid support arms adapted to extend medially and laterally along opposite sides of a patient's limb; first and second limb-contacting plates of arcuate transverse cross-section connected to said arms; said first and second limb-contacting plates having concave inner surfaces disposed in facing relation for engaging medial and lateral sides, respectively, of the limb; and first and second traction plates associated with said limb-contacting plates, with said first traction plate being disposed medially outwardly relative to said first limb-contacting plate and said second traction plate being disposed laterally outwardly relative to said second limb-contacting plate; each traction anterior and posterior wing portions extending plate having a pair of anteriorly and posteriorly relative to one of said support arms and being spaced outwardly from the limb-contacting plate associated therewith; said wing portions including hinge means for allowing spring-like inward flexing of said wing portions, the span of said wing portions of each traction plate being substantially less than the anterior-posterior dimension of said associated limb-contacting plate; and flexible strap means in the form of anterior and posterior straps for separately joining said anterior wing portions of the respective traction plates and said posterior wing portion of said plates for securing said support arms along opposite sides of a patient's limb.

2. The limb brace/immobiliser of claim 1 in which each support arm has a straight distal portion of uniform cross sectional outline; each limb-contacting plate being slidably mounted on one of said straight distal portions for slidable adjustment therealong; and locking means for locking each of said limb-contacting plates in a selected position of adjustment along the support arm on which it is slidably mounted.

3. The limb brace/immobiliser of claim 2 in which said straight distal portion of each support arm is provided with a longitudinal slot; said locking means comprising a screw having a shank extending through said slot and a locking turnwheel threadedly carried by said shank.

4. The limb brace/immobiliser of claims 1 or 2 in which said traction plates are each formed of stiff but flexible thermoplastic material.

5. The limb brace/immobiliser of claim 4 in which each traction plate is formed of one piece and includes a central portion disposed between and integral with said wing portions; said central portion being elongate in the direction of said support arm and merging with said wing portions along a pair of parallel integral hinge zones disposed anteriorly and posteriorly in relation to said support arm.

6. The limb brace/immobiliser of claim 5 in which each of said wing portions of each traction plate angles outwardly away from said central portion and said limb-contacting plate when said traction plate is in an untensioned state.

7. The limb brace/immobiliser of claim 5 in which each traction plate is formed as an integral part of the limb-contacting plate associated therewith.

8. The limb brace/immobiliser of claim 5 in which each traction plate is a discrete component secured by connecting means to its associated limb-contacting plate.

9. The limb brace/immobiliser of claims 1 or 2 in which said limb-contacting plates are formed of thin and stiff but flexible thermoplastic material.

10. The limb brace/immobiliser of claim 9 in which a cushioning layer of soft, compressible material extends along the inner surface of each limb-contacting plate.

* * * * *